United States Patent [19]
Palmer

[11] Patent Number: 5,694,922
[45] Date of Patent: Dec. 9, 1997

[54] SWIVEL TUBE CONNECTIONS WITH HERMETIC SEALS

[75] Inventor: Darrel R. Palmer, Sandy, Utah

[73] Assignee: Ballard Medical Products, Draper, Utah

[21] Appl. No.: 293,009

[22] Filed: Aug. 19, 1994

Related U.S. Application Data

[63] Continuation-in-part of Ser. No. 245,333, May 18, 1994, abandoned.

[51] Int. Cl.[6] .................... A62B 9/04; A62B 9/06; A61M 16/00
[52] U.S. Cl. .................... 128/202.27; 128/207.14; 128/204.18; 128/912; 128/DIG. 26
[58] Field of Search .............. 128/205.12, 205.19, 128/207.14, 911, 912, DIG. 26, 202.27, 204.18; 604/163, 171, 192, 263, 267

[56] References Cited

U.S. PATENT DOCUMENTS

| | | | |
|---|---|---|---|
| 113,503 | 4/1871 | Dinnen . | |
| D. 272,651 | 2/1984 | Mahurkar | D24/54 |
| D. 288,963 | 3/1987 | Jinotti | D24/53 |
| D. 312,880 | 12/1990 | Bodai et al. | D24/53 |
| 1,120,549 | 12/1914 | Schellberg . | |
| 1,214,941 | 2/1917 | Morris et al. . | |
| 1,463,735 | 7/1923 | Varrieur | 251/100 |
| 1,917,981 | 7/1933 | Kindl | 251/95 |
| 1,944,553 | 1/1934 | Freund | 128/229 |
| 2,187,586 | 1/1940 | Hooper | 128/224 |
| 2,212,334 | 8/1940 | Wallerich | 604/780 |
| 2,289,721 | 7/1942 | Mueller | 251/335.2 |
| 2,291,563 | 7/1942 | Rotter et al. | 251/74 |
| 2,538,215 | 1/1951 | Stack | 128/227 |
| 2,584,450 | 2/1952 | Holt et al. | 128/207.14 |
| 2,667,682 | 2/1954 | Stone | 27/24 |
| 2,705,959 | 4/1955 | Elmore | 128/351 |
| 2,734,773 | 2/1956 | Irins | 251/335.2 |
| 2,755,060 | 7/1956 | Twyman | 251/342 |
| 2,776,105 | 1/1957 | Schmitz | 251/335.2 |
| 2,812,765 | 11/1957 | Tofflemire | 128/276 |
| 2,893,395 | 7/1959 | Buck | 128/349 |
| 2,895,708 | 7/1959 | Palumbo | 251/77 |
| 2,912,982 | 11/1959 | Barsky | 128/912 |
| 2,924,232 | 2/1960 | Michaels | 137/315 |
| 2,937,643 | 5/1960 | Elliot | 128/214 |
| 3,017,880 | 1/1962 | Brook | 128/29 |
| 3,039,463 | 6/1962 | Dickey, Jr. et al. | 604/280 |
| 3,070,132 | 12/1962 | Sheridan | 604/280 |

(List continued on next page.)

FOREIGN PATENT DOCUMENTS

| | | | |
|---|---|---|---|
| 560910 | 7/1924 | France . | |
| 3307517 | 8/1984 | Germany | A61M 1/00 |
| 8102675 | 10/1981 | WIPO | 128/207.15 |

OTHER PUBLICATIONS

"Side Eye Position", a report concerning suction kits and catheters; Davol Products (undated).
Cathmark, Item of Literature (date unknown).

(List continued on next page.)

Primary Examiner—Kimberly L. Asher
Attorney, Agent, or Firm—Workman Nydegger Seeley

[57] ABSTRACT

Apparatus and methods are disclosed by which a closed ventilating system accommodates multiple access to the respiratory system of an intubated medical patient without compromising the closed character of the system. Access to the respiratory system through one or more access sites of the closed system apparatus is provided at proximal adapter ports to ventilate the lungs of the patient with gas or gases, to aspirate secretions from the lungs, to oxygenate the lungs to eliminate or reduce residual $co_2$ therefrom, to visually inspect selected parts of the respiratory system, to sample sputum and gases, to sense parameters such as flow rates, pressure, and temperature, to flush with washing solution, and/or to administer medication, gases, and/or lavage. A distal swivel fitting provides multiple sealing sites by which entry of atmosphere is prevented.

15 Claims, 3 Drawing Sheets

U.S. PATENT DOCUMENTS

| | | | |
|---|---|---|---|
| 3,104,090 | 9/1963 | Callahan, Jr. | 251/278 |
| 3,175,557 | 3/1965 | Hammond | 128/207.14 |
| 3,207,472 | 9/1965 | Seltsam | 251/331 |
| 3,322,126 | 5/1967 | Rusch et al. | 128/351 |
| 3,335,723 | 8/1967 | Waldman, Jr. | 128/214.4 |
| 3,363,629 | 1/1968 | Kuhn | 604/281 |
| 3,402,500 | 9/1968 | Dryden | 128/207.16 |
| 3,444,860 | 5/1969 | Harrell | 128/349 |
| 3,461,877 | 8/1969 | Morch | 128/351 |
| 3,485,234 | 12/1969 | Stevens | 604/281 |
| 3,508,554 | 4/1970 | Sheridan | 604/280 |
| 3,517,669 | 6/1970 | Buono et al. | 128/276 |
| 3,584,834 | 6/1971 | Reid et al. | 251/335.2 |
| 3,595,445 | 7/1971 | Burford et al. | 222/213 |
| 3,605,750 | 9/1971 | Sheridan et al. | 604/280 |
| 3,612,038 | 10/1971 | Halligan | 604/281 |
| 3,614,057 | 10/1971 | Hospe | 251/251 |
| 3,628,532 | 12/1971 | Magrath | 128/145.8 |
| 3,633,758 | 1/1972 | Moise | 604/280 |
| 3,719,737 | 3/1973 | Vaillancourt | 604/281 |
| 3,730,179 | 5/1973 | Williams | 128/145.5 |
| 3,734,094 | 5/1973 | Calinog | 128/2.06 |
| 3,757,771 | 9/1973 | Ruegg et al. | 128/2.1 E |
| 3,774,604 | 11/1973 | Danielsson | 128/214.4 |
| 3,788,326 | 1/1974 | Jacobs | 128/305 |
| 3,794,026 | 2/1974 | Jacobs | 128/145.8 |
| 3,825,001 | 7/1974 | Bennet et al. | 128/214.4 |
| 3,831,629 | 8/1974 | Mackal et al. | 604/99 X |
| 3,885,561 | 5/1975 | Cami | 604/280 |
| 3,894,540 | 7/1975 | Bonner, Jr. | 128/349 R |
| 3,911,919 | 10/1975 | Raitte | 128/276 |
| 3,920,023 | 11/1975 | Dye et al. | 604/281 |
| 3,935,857 | 2/1976 | Co | 604/281 |
| 3,937,220 | 2/1976 | Coyne | 604/119 |
| 3,991,762 | 11/1976 | Radford | 128/276 |
| 4,015,336 | 4/1977 | Johnson | 32/33 |
| 4,022,219 | 5/1977 | Basta | 128/351 |
| 4,027,659 | 6/1977 | Slingluff | 604/280 |
| 4,032,106 | 6/1977 | Schieser et al. | 251/335.2 |
| 4,036,210 | 7/1977 | Campbell et al. | 128/2 F |
| 4,047,527 | 9/1977 | Kelsen | 128/229 |
| 4,050,667 | 9/1977 | Kossett | 604/281 |
| 4,052,990 | 10/1977 | Dodgson | 128/207.14 |
| 4,062,363 | 12/1977 | Bonner, Jr. | 128/349 |
| 4,081,176 | 3/1978 | Johnson | 251/342 |
| 4,119,101 | 10/1978 | Igich | 128/351 |
| 4,122,591 | 10/1978 | Kramann et al. | 29/157 R |
| 4,152,017 | 5/1979 | Abramson | 128/207.14 |
| 4,170,946 | 10/1979 | Wu | 128/349 R |
| 4,193,406 | 3/1980 | Jinotti | 128/204.18 |
| 4,212,300 | 7/1980 | Meals | 128/276 |
| 4,214,593 | 7/1980 | Imbruce et al. | 128/748 |
| 4,225,371 | 9/1980 | Taylor et al. | 156/652 |
| 4,235,232 | 11/1980 | Spaven et al. | 128/214.4 |
| 4,240,417 | 12/1980 | Holever | 128/912 |
| 4,245,636 | 1/1981 | Sparks et al. | 128/214 R |
| 4,256,099 | 3/1981 | Dryden | 128/200.26 |
| 4,275,724 | 6/1981 | Behrstock | 604/281 |
| 4,280,680 | 7/1981 | Payne | 251/335.2 |
| 4,300,550 | 11/1981 | Gandi et al. | 128/207.18 |
| 4,324,239 | 4/1982 | Gordon et al. | 128/274 |
| 4,326,520 | 4/1982 | Alley | 128/214.4 |
| 4,327,720 | 5/1982 | Bronson | 128/207.14 |
| 4,327,723 | 5/1982 | Frankhouser | 128/214.4 |
| 4,327,735 | 5/1982 | Hampson | 128/348 |
| 4,333,451 | 6/1982 | Paluch | 128/205.12 |
| 4,351,328 | 9/1982 | Bodai | 128/202.16 |
| 4,354,490 | 10/1982 | Rogers | 128/213 |
| 4,356,610 | 11/1982 | Hon et al. | 29/157 |
| 4,359,204 | 11/1982 | Williams | 281/331 |
| 4,387,879 | 6/1983 | Tauschinski | 251/149.1 |
| 4,397,442 | 8/1983 | Larkin | 251/342 |
| 4,414,999 | 11/1983 | Basta | 137/240 |
| 4,416,273 | 11/1983 | Grimes | 128/207 |
| 4,426,062 | 1/1984 | Bowrom | 251/7 |
| 4,432,759 | 2/1984 | Gross et al. | 604/411 |
| 4,440,370 | 4/1984 | Sullivan | 251/117 |
| 4,451,257 | 5/1984 | Atchley | 604/119 |
| 4,454,887 | 6/1984 | Kruger | 128/772 |
| 4,456,223 | 6/1984 | Ebling | 251/342 |
| 4,457,487 | 7/1984 | Steigerwald | 251/117 |
| 4,459,982 | 7/1984 | Fry | 128/204.23 |
| 4,464,175 | 8/1984 | Altman et al. | 604/99 |
| 4,469,483 | 9/1984 | Becker et al. | 128/DIG. 21 |
| 4,475,548 | 10/1984 | Muto | 128/207.14 |
| 4,497,468 | 2/1985 | Hubbard et al. | 251/117 |
| 4,502,482 | 3/1985 | DeLuccia et al. | 128/207.15 |
| 4,510,933 | 4/1985 | Wendt et al. | 128/351 |
| 4,512,765 | 4/1985 | Muto | 604/119 |
| 4,517,979 | 5/1985 | Pecenka | 128/325 |
| 4,534,542 | 8/1985 | Russo | 251/342 |
| 4,537,387 | 8/1985 | Danby et al. | 251/311 |
| 4,545,367 | 10/1985 | Tucci | 128/1 R |
| 4,551,146 | 11/1985 | Rogers | 604/403 |
| 4,569,344 | 2/1986 | Palmer | 128/207.16 |
| 4,585,440 | 4/1986 | Tchervenkov et al. | 604/164 |
| 4,595,005 | 6/1986 | Jinotti | 128/205.24 |
| 4,607,635 | 8/1986 | Heyden | 128/207.15 |
| 4,610,469 | 9/1986 | Wolff-Mooij | 285/260 |
| 4,613,323 | 9/1986 | Norton et al. | 604/43 |
| 4,632,112 | 12/1986 | Matthews | 128/305.3 |
| 4,634,433 | 1/1987 | Osborne | 604/171 |
| 4,637,389 | 1/1987 | Heyden | 128/207.15 |
| 4,638,539 | 1/1987 | Palmer | 29/157 R |
| 4,646,733 | 3/1987 | Stroh et al. | 128/207.16 |
| 4,655,752 | 4/1987 | Honkanen et al. | 604/256 |
| 4,669,463 | 6/1987 | McConnell | 128/207.14 |
| 4,671,291 | 6/1987 | Wilson | 604/280 |
| 4,673,393 | 6/1987 | Suzuki et al. | 604/167 |
| 4,674,496 | 6/1987 | Svadjian et al. | 128/207.16 |
| 4,696,296 | 9/1987 | Palmer | 128/207.16 |
| 4,696,305 | 9/1987 | Von Berg | 128/673 |
| 4,703,775 | 11/1987 | Pastrone | 137/625.3 |
| 4,704,111 | 11/1987 | Moss | 604/280 |
| 4,762,125 | 8/1988 | Leiman et al. | 128/207.15 |
| 4,781,702 | 11/1988 | Herrli | 604/244 |
| 4,796,615 | 1/1989 | Bullock | 128/202.27 |
| 4,805,611 | 2/1989 | Hodgkins et al. | 128/207.14 |
| 4,810,241 | 3/1989 | Rogers | 604/29 |
| 4,821,714 | 4/1989 | Smelser | 128/207.14 |
| 4,825,859 | 5/1989 | Lambert | 128/202.16 |
| 4,827,921 | 5/1989 | Rugheimer | 128/202.27 |
| 4,834,726 | 5/1989 | Lambert | 604/281 |
| 4,836,199 | 6/1989 | Palmer | 128/207.16 |
| 4,838,255 | 6/1989 | Lambert | 128/202.16 |
| 4,838,879 | 6/1989 | Tanabe et al. | 604/280 |
| 4,850,350 | 7/1989 | Jackson | 128/207.16 |
| 4,872,579 | 10/1989 | Palmer | 128/205.19 |
| 4,886,496 | 12/1989 | Conoscenti et al. | 604/96 |
| 4,929,426 | 5/1990 | Bodai et al. | 422/98 |
| 4,935,010 | 6/1990 | Cox et al. | 604/122 |
| 4,936,542 | 6/1990 | Beard | 251/331 |
| 4,938,741 | 7/1990 | Lambert | 604/19 |
| 4,967,743 | 11/1990 | Lambert | 128/207.15 |
| 4,969,878 | 11/1990 | Schmidt et al. | 604/264 |
| 4,979,765 | 12/1990 | Bartholomew | 285/93 |
| 4,981,466 | 1/1991 | Lambert | 604/19 |
| 4,995,386 | 2/1991 | Ng | 128/205.19 |
| 4,995,387 | 2/1991 | Jinotti | 128/205.24 |
| 5,009,391 | 4/1991 | Steigerwald | 251/149.1 |
| 5,057,093 | 10/1991 | Clegg et al. | 604/283 |
| 5,060,646 | 10/1991 | Page | 128/207.14 |

| | | | |
|---|---|---|---|
| 5,062,420 | 11/1991 | Levine | 128/204.18 |
| 5,083,561 | 1/1992 | Russo | 128/207.16 |
| 5,088,486 | 2/1992 | Jinotti | 128/207.14 |
| 5,101,820 | 4/1992 | Christopher | 128/204.18 |
| 5,107,829 | 4/1992 | Lambert | 128/202.16 |
| 5,125,893 | 6/1992 | Dryden | 604/54 |
| 5,133,345 | 7/1992 | Lambert | 128/202.16 |
| 5,134,996 | 8/1992 | Bell | 128/207.14 |
| 5,139,018 | 8/1992 | Brodsky et al. | 128/207.14 |
| 5,140,983 | 8/1992 | Jinotti | 128/207.14 |
| 5,158,569 | 10/1992 | Strickland et al. | 604/283 |
| 5,215,522 | 6/1993 | Page et al. | 604/33 |
| 5,255,672 | 10/1993 | Jinotti | 128/200.6 |
| 5,277,177 | 1/1994 | Page et al. | 128/200.26 |
| 5,309,902 | 5/1994 | Kee et al. | 128/202.17 |
| 5,325,851 | 7/1994 | Reynolds et al. | 128/207.16 |
| 5,333,606 | 8/1994 | Schneider et al. | 128/200.24 |
| 5,333,607 | 8/1994 | Kee et al. | 128/204.18 |
| 5,337,780 | 8/1994 | Kee | 127/381 |
| 5,357,946 | 10/1994 | Kee et al. | 128/200.24 |
| 5,368,017 | 11/1994 | Sorenson et al. | 128/200.26 |

OTHER PUBLICATIONS

Superior Brochure "Continuous Ventilating SUction System" 1984.

Superior Advertisement, "Infection Control Valve Suction Catheter" 1984.

Suctioning of Left Bronchial Tree in the Intubated Adult, Care Medicine, Kamiaru; 092, vol. 10, #1, 1982, pp. 43–45.

Evaluation of Selective Brochial Suctioning Techniques Used for Infants and Children. Anesthesiology, 48:379–380, 1978.

ACMI Catalog, pp. 31–35, Copyright 1960, Pelham, NY.

Prevention of Hypoxic Complication—1968, Surgery, vol. 63, No. 4, pp. 586–587.

"Sterile Suctioning With Bare Hands", The Nation's Hospitals and Diagnostic Laboratories, Fall 1975.

Comparison of Tracheobronchial Suction Catheters in Humans, Chest, vol. 69, pp. 179–181, Feb. 1976.

Selective Tracheobronchial Aspiration, Thorax, 32; 346–348, 1977.

Efficon Trach Care Brochure and Price List, Apr. 15, 1978.

A New Controllable Suction Catheter for Blind Cannulation of the Main Stem Bronchi, Critical Care Medicine, vol. 6, No. 5, Sep.–Oct. 1978.

Disposable Suction Catheter, Nursing, May 1979, p. 70.

Evaluation of Selective Bronchial Suctioning in the Adult, Critical Care Medicine, vol. 8, No. 12, 1980.

Selective Bronchial Suctioning in the Adult Using a Curved–Tipped Catheter with a Guide Mark, Critical Care Medicine, vol. 10, No. 11, Nov. 1982, Kubota et al.

Device for Determining Location of an Endotracheal Catheter Tip, Critical Care Medicine, vol. 12, No. 2, Feb. 1984.

The Bear NVM–1 Neonatal Volume Monitor, Oct. 1986 (citing U.S. 4,363,238). Form #90045, Riverside, CA.

Article entitled Tracheal Gas Insufflation During Pressure Control Ventilation By A. Nahum, S. A. Ravenscraft, G. Nakos, W. C. Burke, A. B. Adams, T. W. Marcy, and J. J. Marini, dated Feb. 21, 1992.

Article entitled Tracheal Gas Insufflation Augments CO2 Clearance During Mechanical Ventilation, By Sue Ravenscraft and others, Am. Rev. Respir. Dis., vol. 148, pp. 345–351, 1993.

Article in the ASAIO Journal 1993 by A. Raszynski and others entitled Rescue From Pediatric ECMO With Prolonged Hybrid Intratracheal Pulmonary Ventilation.

Article in The Journal of Critical Illness, Nov. 1988, entitled The Technique of Endotracheal Suctioning in Intubated Patients by Donald G. Brown, R.R. T. and Robert B. Schoene, M.D.

Article in Ann. Surg., Jul. 1971, vol. 174, No. 1, To Fell, M.D., F. W. Cheney, M.D., Prevention of Hypoxia During Endotracheal Suction.

Article in Heart and Lung, Mar. 1986, vol. 15, No. 2, entitled Minimizing Hypoxia Due to Endotracheal Suctioning: A Review of The Literature, By Cynthia A. Barnes, RN, MSN, CCRN, and Karin T. Kirchhoff, Ph.D., RN.

Article in Clinical Workshop, vol. 31, No. 5, Nov. 1969, entitled Avoidance of Hypoxemia During Endotracheal Suction, by Bruno J. Urban, M.D., and Stanley W. Weitzner, M.D.

Article in Heart and Lung entitled a Review and Critique of the Literature on Preoxygenation for Endotracheal Suctioning, by Barbara Riegel, MN, RN, CS, and Terri Forshee, RN, MSN, CCRN, dated Sep. 1985, vol. 14.

1988 Publication by Bob Demers entitled Complications of Suctioning: Their Porphylaxis and Treatment.

Review of Respiratory Disease, vol. 148, 1993, pp. 564–568.

Article by Eckhard E. Muller and others entitled How to Ventilate Lungs as Small as 12.5% of Normal: The New Technique of Intratracheal Pulmonary Ventilation, dated 1993, Pediatric Research. pp. 606–610.

Article by Laurent Brochard and others entitled Constant Flow Insufflation Prevents Arterial Oxygen Desaturation During Endotracheal Suctioning, dated Feb. 20, 1990., AM Rev. Respir p. 15 1991; 144; 395–400.

Article in Respiratory Care, May 1993, vol. 38, No. 5, entitled Endotracheal Suctioning of Mechanically Ventilated Adults and Children with Artificial Airways.

Article in Heart and Lung, vol. 10, No. 6, dated Nov.–Dec. 1981, entitled Oxygen insufflation During Endotracheal Suctioning by Ellen Ann Langrehr, RN, MS, CCRN, and others.

Ballard Medical Products literature on the Super–Vac, Form #20082, Feb. 1992, Draper, UT, 84020.

Ballard Medical Products literature on Trach Care, Form #20108, May 1993, Draper, UT 84020.

Ballard Medical Products literature (Cat. No. 121) on Ready Care Oral Suction, Form #20046, Oct. 91, Draper, UT, 84020.

Ballard Medical Products literature on Safety Drain, Form #20052, Apr. 1991, Draper, UT, 84029.

Ballard Medical Products literature on Trach Care Directional Tip, Form #20039A, Apr. 1989, Midvale, UT, 84047.

Article in Am. Rev. Respir. Dis., vol. 148, pp. 562–568, 1993, entitled Modes of Tracheal Gas Insufflation by William C. Burke and others.

Literature on the Skinner 3000 Series, undated.

Article in the Am. Rev. Respir. Dis., vol. 147, pp. 1590–1594, 1993, entitled Small Bore Nozzle Extensions to Improve the Delivery Efficiency of Drugs From Metered Dose Inhalers: Laboratory Evaluation, by Ralph W. Niven and others.

Ballard Medical Products literature on BAL CATH, Form 20117, Oct. 1993, Draper, UT 84020.

Exhibit "A"—Product entitled Swivel Elbow, Product DHD 66–1995, available from DHD, Availability date unknown.

Exhibit "B"—Product known as Bodai Suction–Safe Swivel Y, available from Sontek Medical, availability date unknown.

Exhibit "C"—Elbow Adapter available from Intersurgical, Inc., availability date unknown.

Exhibit "D"—top photo, commercially available elbow, source unknown, availability date unknown.

Exhibit "D"—bottom photo—commercially available slit valve insert, source unknown, availability date unknown.

Exhibit "F"—Linear adapter with one swivel end, available from Concord, availability date unknow.

Exhibit "G"—Product identified as Jet Ventilator Adapter available from Portex, availability date unknown.

Exhibit "H"—Example of one of several similar irrigation vials available from a plurality of commercial sources, availability date unknown.

Article dated Jul. 12, 1988, by James I. Couser, Jr. and Barry J. Make, entitled Transtracheal Oxygen Decreases Inspired Minute Ventilation, AM Rev. Respir Dis, 1989, 139:627–631.

Article entitled the effects of Apnea, Endotracheal Suction, and Oxygen Insufflation, Alone and in Combination, Upon Arterial Oxygen Saturation in Anesthetized Patients, By Antonia Boba, M.D., and others. J. Lab. & Clin. Med., May 1959, vol. 53, #5.

Article in *American Journal of Critical Care*, vol. 1, No. 3, entitled Preventing Hypoxemia and Hemodynamic Compromise Related to Endotracheal Suctioning by Joan Mancinelli–Van Atta, RN, MSN, and Susan L. Beck, RN, Ph.D., pp. 62–79.

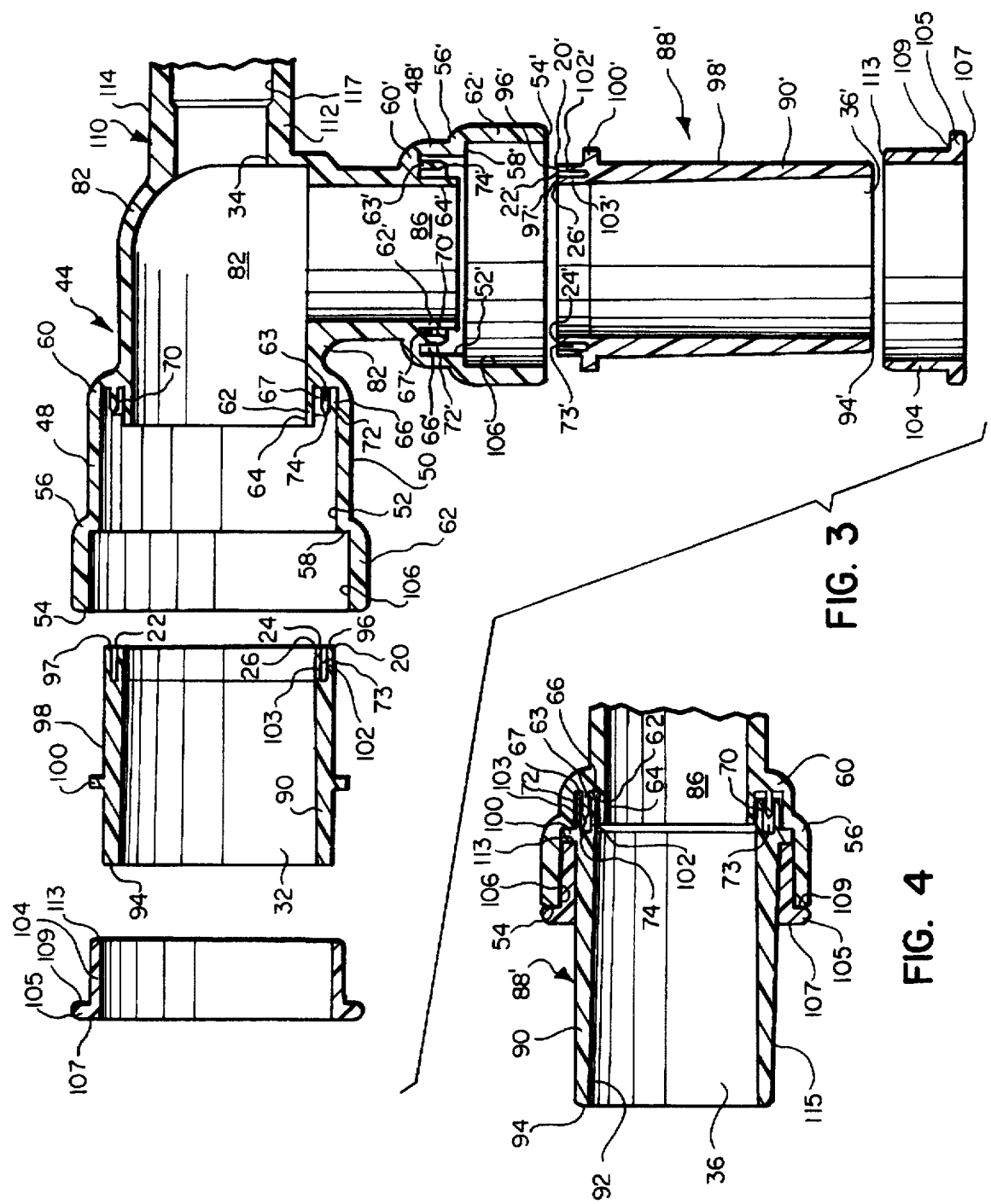

SWIVEL TUBE CONNECTIONS WITH HERMETIC SEALS

RELATED APPLICATIONS

This application is a continuation-in-part of U.S. patent application Ser. No. 08/245,333 filed May 18, 1994, now abandoned, entitled "Medical Multiple Access Low Dead Space Anti-Microbial Aspirating/Ventilating Closed System Improvements and Methods".

FIELD OF INVENTION

The inventions disclosed herein relate generally to improved medical care for intubated patients, and more particularly to novel low dead space improvements, and related methods, for ventilating, aspirating, monitoring, sampling, and providing therapeutic delivery to the respiratory tract of intubated medical patients, including infants, adolescents, and adults.

BACKGROUND

Respiratory patient care is a dynamically developing field in medicine, ranging in its needs from infants to the aged. The range of respiratory ailments, both temporary and permanent, to which such patients are subjected are many and varied. The frontier of medical knowledge is advancing and recommended treatments have become a blend of old and more recent discoveries.

Most problems now center or focus on multiple needs of the patient and accommodation of multiple treatments, some to be performed at the same time. The lack of equipment to facilely, efficiently, and safely accomplish the multiple therapies in the best interest of the patient has been and continues to be a concern. Other equipment problems also exist which concern preventing cost-oriented, unsafe extended use of ventilating, aspirating, and other respiratory access apparatus, reliability during use, quick and reliable removal and exchange of spent aspirating and ventilating devices without compromising the quality of health care provided to the patient, avoiding intentional or inadvertent conversion from a closed system to an open system, prevention of stress and/or occlusion of flow passageways to and from the patient's respiratory system, avoidance of a large inventory of a variety of incompatible products, providing easy, fail-safe access for multiple purposes.

By way of an example only, with low lung capacity patients, such as premature babies and adults suffering from emphysema, one problem is the removal of accumulated lung secretions without starving the patient for oxygen (thereby causing undesirable side effects) during the secretion removal process.

Sight must not be lost as to the deficiencies in prior proposals in terms of risks created for the health care provider. Largely, proposals of the past have ignored the needs of the health care provider to attain a reasonable measure of protection from contamination by the patient.

Providing apparatus and methodology having the capacity to promptly, efficiently, safely, and cost effectively address the health care needs of intubated patients across the entire spectrum of respiratory ailments comprises, prior to the present invention, a largely unresolved need. The range of procedures comprise: ventilating, aspiration, oxygenation, sampling, visual inspection, in-line sensing, pressure monitoring, flushing, and medication and/or lavage. Better protection for the health care provider has been a long-term unsatisfied need.

BRIEF SUMMARY AND OBJECTS OF THE PRESENT INVENTION

In brief summary, the present invention substantially alleviates the aforesaid problems of the prior art and comprises apparatus and methods by which a closed ventilating system accommodates multiple access to the respiratory system of an intubated medical patient without compromising the closed character of the system. Access to the respiratory system through one or more access sites of the closed system apparatus is provided to ventilate the lungs of the patient with gas or gases, to aspirate secretions from the lungs, to oxygenate the lungs to eliminate or reduce residual $CO_2$ therefrom, to visually inspect selected parts of the respiratory system, to sample sputum and gases, to sense parameters such as flow rates, pressure, and temperature, to flush with washing solution, and/or to administer medication, gases, and/or lavage.

The system can be unitized into severable and disposable components which are cost effective and accommodate good health care practices while promoting limitations on duration of use well within appropriate medical tolerances. Quick removal and replacement of discarded components is accommodated without introduction of additional risks to the patient. The technology of the present invention has substantial universal application to all respiratory patients, ranging from infants to the aged. Swivel fittings or adapters, in the form of an elbow or other configuration, provide dual or multiple fail safe sealing structure.

With the foregoing in mind, it is a primary object of the present invention to substantially alleviate problems of the prior art in the field of respiratory care for medical patients.

It is an additional dominant object of the present invention to provide apparatus and related methods by which a closed ventilating system is able to accommodate multiple access to the respiratory system of an intubated medical patient.

An additional paramount object is the provision of novel apparatus and related methods by which a closed ventilating system accommodates multiple access to the respiratory system of an intubated medical patient without compromising the closed character of the system.

An additional object of the present invention is the provision of access through one or more access sites in a closed system respiratory apparatus to accommodate ventilating of the lungs of the patient with gas or gases, to aspirate secretions from the lungs, to oxygenate the lungs to eliminate or reduce residual carbon dioxide therefrom, to visually inspect selected parts of the respiratory system, to sample sputum and gases, to sense parameters such as flow rates, pressure, and temperature, to flush with washing solution and/or to administer medication, gases, and/or lavage, and related methods.

An additional significant object is the provision of a closed respiratory health care system unitized into severable and disposable components which are cost effective and accommodate good health care practices while promoting limitations on duration of use well within appropriate medical tolerances.

It is an additional valuable object to provide for quick removal and replacement of discardable components toward the end of their useful life in a respiratory health care system and to accommodate such without introduction of additional risks to the patient.

It is another dominant object to provide a respiratory health care system and related methods which has substantial universal application to all respiratory patients ranging from infants to the aged.

A further important object of the present invention is to provide features in a respiratory health care system which avoid imposition of stress on the components and prohibit occlusion of flow pathways.

It is a prominent object of the present invention to provide respiratory health care systems and related methods which accommodate simultaneous access to and treatment within the respiratory system of a medical patient.

It is a further object of the present invention to provide novel respiratory health care systems and related methods having minimal dead space.

It is another paramount object to provide novel fittings and/or adapters which accommodate stress relief rotation and/or structure dual or multiple fail safe sealing between the closed interior of the fitting or adapter and the atmosphere, and related methods.

These and other objects and features of the present invention will be apparent from the detailed description taken with reference to the accompanying drawings.

BRIEF DESCRIPTION OF THE DRAWINGS

FIG. 3 is an exploded longitudinal cross-section through the distal fitting or adapter of FIG. 1, showing the components of the adapter in their disassembler or prior-to-assembly condition;

FIG. 4 is a cross-section of the dual seal features of the distal fitting or adapter of the apparatus of FIG. 1;

DETAILED DESCRIPTION OF THE ILLUSTRATED EMBODIMENT

Figure 1:
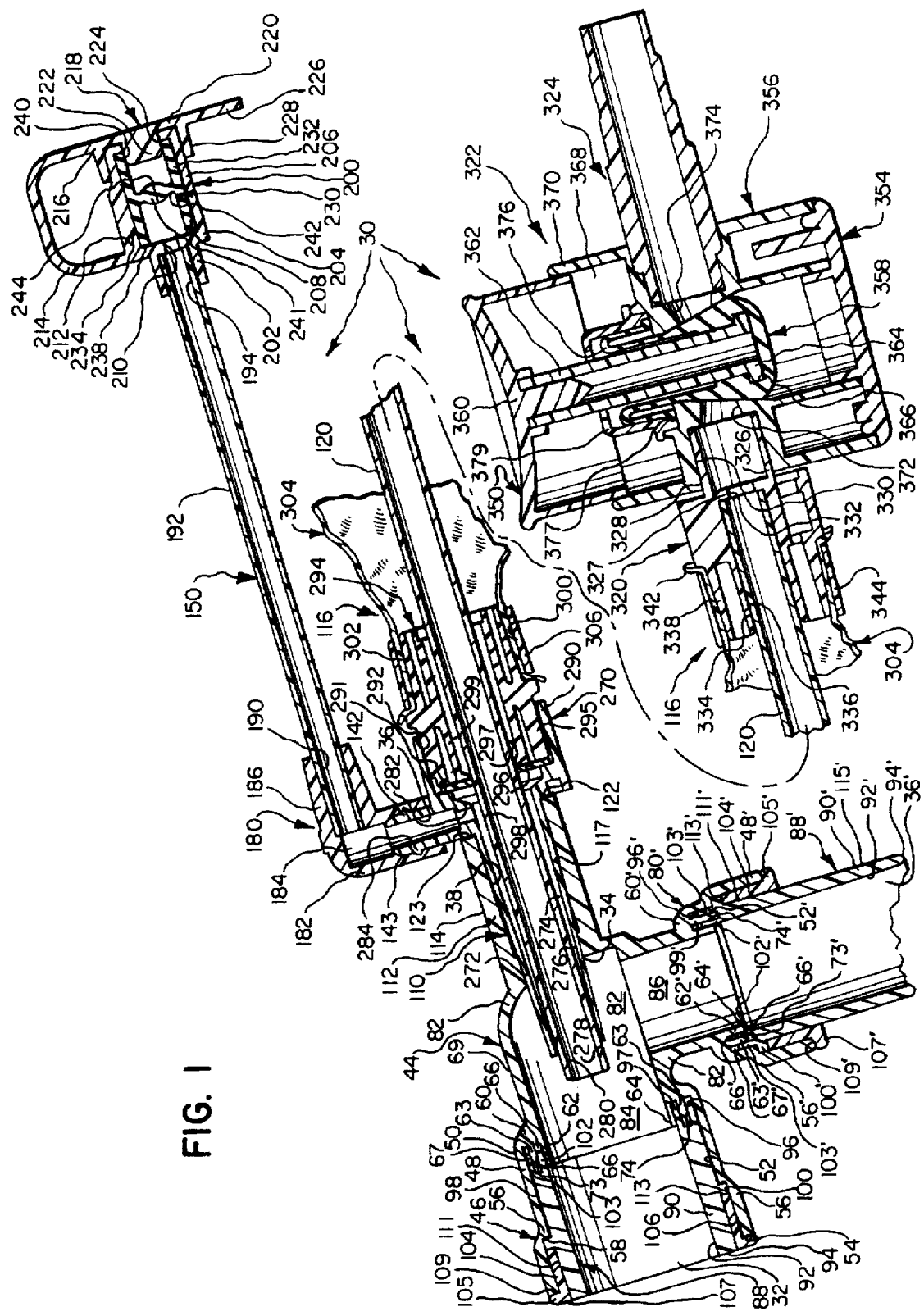
FIG. 1 is a fragmentary cross-section of one aspirating/ventilating apparatus embodying principles of the present invention.

Reference is now made to the drawings wherein like numerals are used to designate like parts throughout. FIG. 1 illustrates in longitudinal cross-section a multi-access apparatus, generally designated 30, for use in conjunction with the respiratory tract of an intubated medical patient ranging from infants to the aged. The apparatus 30 comprises a single distal access port 32 and a plurality of proximal access ports 34 and 36. For example only, access ports 32 and 36 accommodate continual cyclic patient ventilation, independent of pursuit by the health care provider of any other patient respiratory access procedure. Access port 34 accommodates selective insertion and subsequent removal of an aspirating catheter assembly, the catheter tube of which may be used to remove secretions from the lungs, to replace residual carbon dioxide in the lungs with oxygen, to accommodate entry of temperature or pressure monitoring instruments or to accommodate obtaining samples of sputum or gases and/or to allow insertion of visual inspection instruments.

The apparatus 30 comprises a tracheal tube adapter, generally designated 44, preferably formed of injection molded rigid medical grade synthetic resinous material, such as acrylic, cyrolite, pebax, polypropylene, or the like. While any suitable adapter shape could comprise the distal fitting of the apparatus 30, the shape illustrated is that of an elbow. Adapter 44 comprises dual fitting, each comprising a hollow female distal bell housing, generally designated 46, which comprises a stepped annular wall 48.

Wall 48 comprises a thickness which is generally uniform, defined by inside and outside surfaces 50 and 52. The distal end of wall 48 is defined by a blunt transverse annular distal edge 54, where the bell housing comprises its largest diameter. Wall 48 comprises a first reduced diameter annular step 56 comprising inside shoulder 58, and a second further reduced diameter annular step 60.

Figure 6:
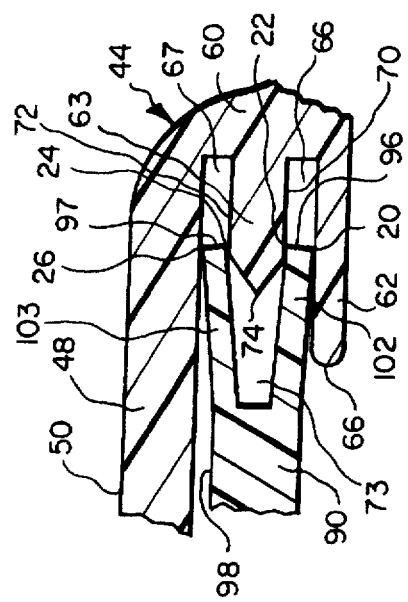
FIG. 6 is an enlarged fragmentary cross-section of the assembled dual seal construction forming a part of the distal adapter or fitting.

Referring also to FIG. 6, annular step 60 defines a trifurcation where dual annular swivel alignment-retaining and sealing walls 62 and 63 extend distally from the juncture sites with wall 48 adjacent step or shoulder 60. Walls 48, 62, and 63, where co-extensive, are separated by blind annular slots 66 and 67 which open distally. Walls 48, 62, and 63 are illustrated as being formed as one-piece. Wall 62 comprises an interior surface 64, illustrated as being of uniform diameter, and a blunt annular transverse distal edge 61. Wall 48 proximal of shoulder 60 comprises exterior annular wall 69. Central wall 63 is annular and comprises inside and outside surfaces 70 and 72, respectively, of uniform diameter. Wall 63 terminates in a converging double beveled or pointed end 74.

Figure 5:
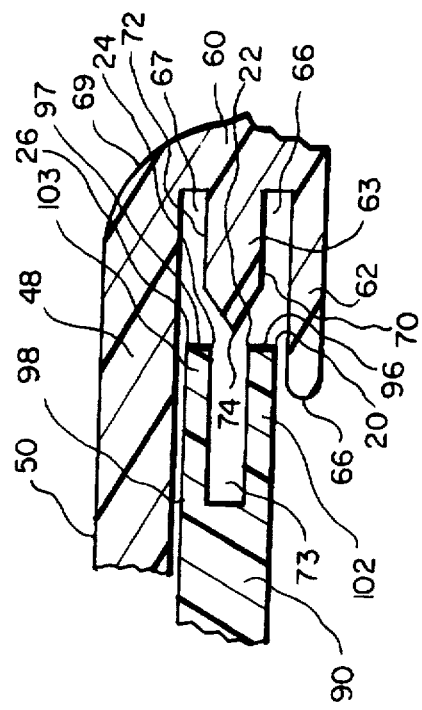
FIG. 5 is an enlarged fragmentary cross-section of the dual seal construction of the distal adapter or fitting prior to assembly.
Figure 2:
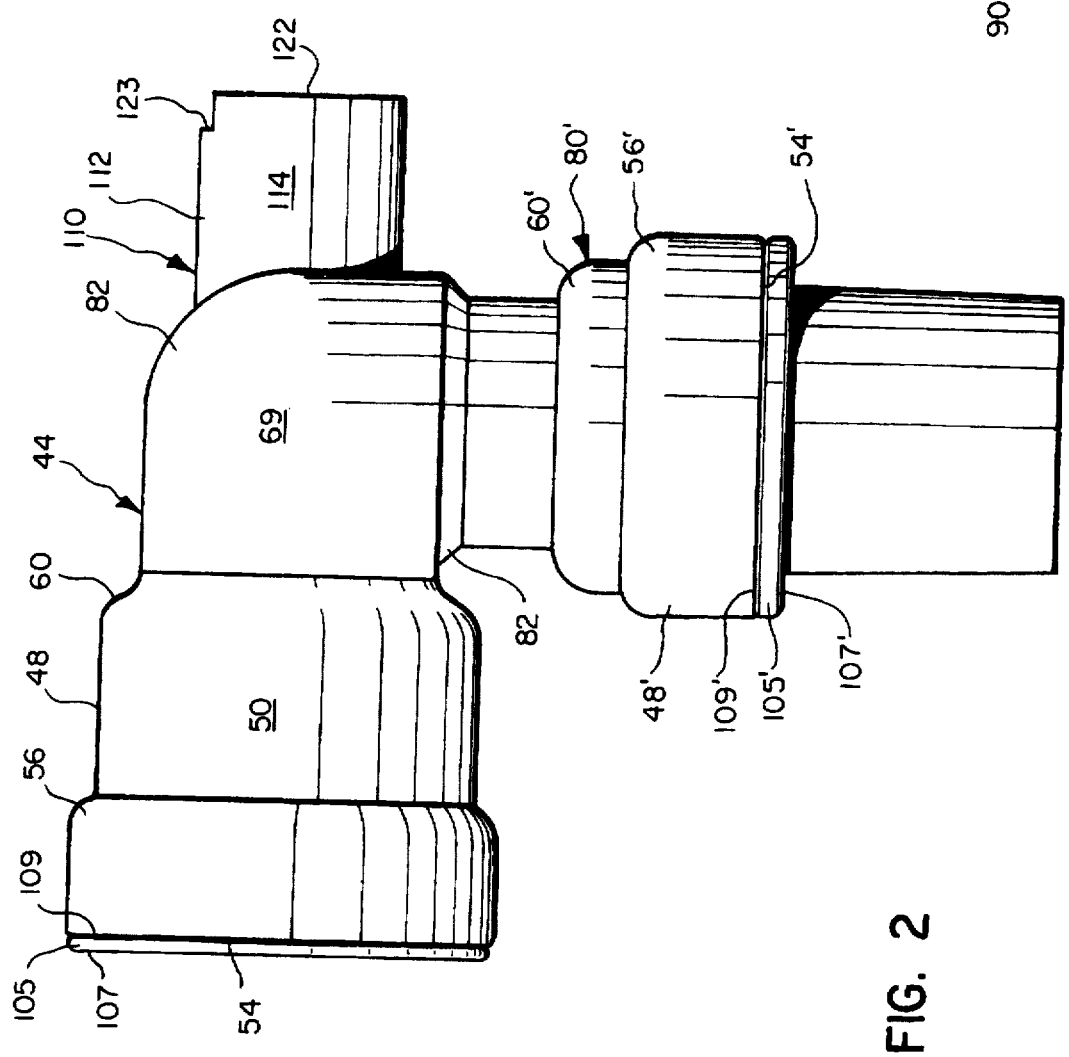
FIG. 2 is a side elevation of the distal fitting or adapter of the apparatus of FIG. 1.

Adapter 44 also comprises a second bell housing, generally designated 80, which is constructed to comprise components substantially the same as bell housing 46, although bell housing 80 is somewhat shorter in its axial length. Accordingly, the parts of bell housing 80 have been enumerated the same as bell housing 46 and no further description is needed for one skilled in the art. Bell housing 80 is illustrated as being disposed generally at 90 degrees to bell housing 46 in the illustrated elbow configuration. The dual or multiple seal structure mentioned above and shown best in enlarged fragmentary cross-section in FIGS. 5 and 6 creates four seal sites 20, 22, 24, and 26 (FIG. 6) at the tips of the blunt edges 96 and 97 of the double male prong 102 and 103 upon entry into female blind slots 66, 67. As illustrated in FIG. 6, as double male prong or sealing ribs 102 and 103 enter female blind slots 66 and 67, they are deflected in a radial direction. This causes them to contact the adjacent walls and form sealing sights 20, 22, 24, and 26.

Wall 62 of bell housing 46 and wall 62 of bell housing 80 merge at site 82, where a passageway 86 comprising port 34 merges with a passageway 84 comprising port 32.

A swivel sleeve, generally designated 88, is rotatably positioned and secured within the bell housing 46. Sleeve 88 comprises an annular wall 90 comprising an interior surface 92, which is generally annular, but may be slightly divergently tapered from left to right, as viewed in FIG. 1, to accommodate a press-fit but removable union with a proximal fitting of a tracheal tube 89, for example, in a manner generally well-known to those skilled in the art. Sleeve 88 also comprises a predetermined length between blunt edge 94 at one end and blunt edges 96 and 97 at the other end. Edge 94 extends distally a short distance beyond edge 54. Edges 96 and 97 extend respectively, into slots 66 and 67, adjacent to the shoulder 60.

Sleeve 88 also comprises an outside surface 98, which is interrupted by an outwardly directed radially-extending retaining flange 100. The location of flange 100 is selected to be adjacent step or shoulder 56 to accommodate rotation contiguous with shoulder 58. Sleeve 88 also comprises a pair of spaced relatively thin integral annular sealing rib or fingers 102 and 103 which sealingly fit into blind slots 66 and 67, respectively, when assembled. Ribs 102 and 103 extend proximally in an axial direction.

When sleeve 88 is assembled into the position illustrated in FIG. 1, the sealing ribs 102 and 103 are, respectively, caused to forcibly engage the annular surfaces defining slots 66 and 67 to thereby hermetically close, at two spaced locations each, the interface between sleeve 88 and bell housing 46.

Sleeve 88 is retained in the position illustrated in FIG. 1 by an annular rigid plastic collar 104 positioned between walls 48 and 90 and distally terminated in a radially directed distal flange 105. The trailing edge 107 of flange 105 is radially flush with edge 94, while leading edge 109 of flange 105 is radially flush with and abuts edge 54. Collar 104 is bonded to surface 106 of wall 48. Thus, collar 104 functions as a bushing with flange 100 rotatably engaging the edges 58 and 113.

Sleeve 88', which is rotatably coupled to bell housing 80, is substantially identical to sleeve 88, being rotatably placed within bell housing 80. Sleeve 88' is enumerated identical to sleeve 88, although it will be readily apparent that the sleeve orientation is reversed, the overall length of sleeve 88 is shorter, the sleeve 88' extends beyond bell housing 80 and the radial flange 100 is positioned closer to slot 63.

Ventilating tubing 89' is compression fit into or over the exposed surface 115 of sleeve 88'. A tracheal fitting 88' is inserted into the hollow of sleeve 88. Sleeve 88' rotates with any rotation imposed upon the connected ventilating tubing or, alternatively, retain an essentially stationary position if and when the adapter 44 is rotated, either intentionally or inadvertently in respect to sleeves 88 and 88'. Thus, twisting and consequential occluding or partial occluding of ventilating tubing is avoided.

Adapter 44 further comprises a proximally-directed barrel, generally designated 110. Proximally-directed barrel 110 comprises an annular wall 112, the exterior surface 114 of which is annular, while the interior surface 117 is illustrated as being slightly tapered divergently in a distal direction to receive, in compression-fit relation, an aspirating catheter cartridge, generally designated 116. Cartridge 116 will be explained in greater detail hereinafter.

The interior surface 117 defines a proximal passageway, the diametral size of which is substantially smaller than either of the two previously described passageways 84 and 86. Wall 112 merges at site 82 with bell housings 44 and 80, respectively, in such a way that the passageway defined by surface 117 merges distally with passageway 84. It should be noted that the longitudinal axis of passageway 84 and the longitudinal access of the passageway defined by wall surface 117 are substantially aligned with each other to accommodate ease of insertion of a slidable aspirating catheter tube 120, forming part of the aspirating catheter cartridge 116. Catheter tube 120 is flexible along its length to accommodate smooth insertion through a tracheal tube, for example, into either lung of the patient for removal of secretions.

Wall 112 terminates in a blunt transverse proximal edge 122 and is formed as one piece with the other components of adapter 44, excluding swivel sleeves 88 and 88' and retainers 104. While not shown, edge 122 may be slotted at 123 to receive a side port of cartridge 116.

The previously mentioned aspirating catheter cartridge or assembly 116 comprises the mentioned aspirating catheter tube 120, illustrated as being of uniform thickness and inside and outside diameter throughout, and a distal fitting, generally designated 270. Fitting 270 comprises a slightly tapered distally-directed wall 272, shown as being in spaced relation to and telescopic surrounding catheter tube 120, catheter tube 120 being illustrated in FIG. 1 in a withdrawn state. A space or chamber 274 exists between the exterior surface of the catheter tube 120 and the interior surface 276 of wall 272. Wall 272 terminates at distal blunt edge 278. Inwardly-directed annular flange 278 defines a central circular opening at surface 280 through which tube 120 contiguously though slidably extends.

Wall 272 is interrupted by transverse opening 282, which is aligned with the hollow interior of a transverse, relatively short hollow male projection 284. Projection 284 is formed as one piece with wall 272. The attachment 150, connected to transverse tube 284, comprises a distal fitting, generally designated 180, which is L-shaped in configuration, as illustrated. A first hollow leg 182 of fitting 180 is force-fit over barb 142 and around the exterior surface 143 of tube 284 as illustrated in FIG. 1. Leg 182 comprises a hollow interior 184 aligned with opening 282 through which liquid may be selectively communicated. Fitting 180 comprises a second hollow leg 186, disposed, as illustrated, at approximately 90° in respect to leg 182. Leg 186 comprises a hollow interior bore 188, disposed at approximately fight angles to passageway 184 into which a distal end 190 of a flow accommodating tube 192 is placed, either in a compression fit relation, or so as to be bonded or plastic welded in position. Tube 192 may be of any desired length.

Attachment 150 comprises, in addition, a proximal fitting, generally designated 200. Proximal fitting 200 comprises a distal boss 202, into which proximal end 194 of tube 192 is either force-fit or secured as by plastic welding, bonding, or the like. Boss 202 merges, at shoulder 204, into an enlarged annular wall 206. Communication between the hollow interior at the proximal end 194 of tube 192 and the hollow interior 208 within wall 206 is accommodated at orifice 210, the diameter of which is illustrated as being smaller than the inside diameter of tube 192. Wall 206 is thicker at region 212, to accommodate connection of a tether 214 so as to avoid risk that the tether 214 will become severed from the wall 206, with which it is formed initially as one piece. Tether 214 connects at site 216 to a press-fit cap, generally designated 218. Cap 218 comprises a proximal wall or flange 220, centrally thicker at 222 to accommodate being press-fit into proximal opening 224 in the fitting 200. The proximal wall 220 comprises an extension 226, which the user may manually grasp to remove the cap 218 from its closed position, which is illustrated in FIG. 1. Cap 218 also comprises an external annular collar 228, the interior diameter of which is slightly less than the exterior diameter of wall 206, accommodating a press-fit union, which can be manually removed when desired, but will not inadvertently separate.

Wall 206 defines a hollow interior cylindrical chamber surrounded by annular surface 208 in which a cylindrically shaped slit valve, generally designated 230, is disposed. In cross-section, slit valve 230 is generally "T"-shaped, as seen in FIG. 1, and comprises an end-to-end length substantially equal to the interior length of cylindrical wall 208. Slit valve 230 may be formed of silicone rubber, KRATON™ silicon rubber, or the like, and comprises an annular wall 232 of uniform thickness throughout, as illustrated, comprising an external surface 234, an internal surface 236, as well as blunt transversely disposed distal and proximal edges 238 and 240.

A contoured radially-directed double dome-shaped central wall or diaphragm 241 expands across and normally closes the space within interior surface 236. Web or wall of diaphragm 230 is necked down at the annular site 242 where diaphragm 240 joins wall 232, as one piece, making annular site 242 the weakest part of wall 240, exclusive of one or more central slits 244. Slit 244 may be of any desired size so as to be capable of receiving a hollow male end of an instrument therethrough, which may be utilized to serve any number of purposes. For example, respiratory medication may be applied through a hollow male projection physically inserted through slit 244, through which the medication may be dispensed under aerosol pressure or by manually-generally pressure, for example. The slit 244 is illustrated as being located both at the center of the slit valve 230 and in the region of greatest thickness of wall 241. By providing a centrally thicker wall accompanied by a peripherally weakened wall, at 242, the periphery yields more readily allowing somewhat of coordinated rotation in the wall at both the periphery 242 and at slit 244 when a male projection is physically forced through and removed from the slit 244 both when there is pressure and when there is no pressure at the interior site of the diaphragm 241. Also, the double domed configuration of the diaphragm 241, with the enlarged lips at the slit 244 enhances a return to the normally closed state upon removal of the male projection.

The attachment 150 of the aspirating catheter cartridge 116 may be used to wash the exterior and interior surfaces of the catheter tube after it is withdrawn from the patient, saline or other suitable wash solution being introduced by a hollow male projection extended through slit 244 and thence along the hollow interior of attachment 150 of catheter cartridge 116 through opening 282 into chamber 274. The contiguous relation between catheter tube 120 and tube 272 near edge 278 limits passing of the wash solution into the chamber 118 and from thence into the respiratory tract of the patient. Used wash solution is evacuated through the hollow of the catheter tube 120 due to suction applied there. Also, lavage may be introduced through attachment 150, in the manner explained above, when the catheter tube 120 is fully or partially inserted, which lavage rum slowly down the catheter tube into the respiratory tract.

The distal fitting 270 comprises an exposed trailing or proximal annular flange 290, which, prior to assembly comprises a collar having a hollow interior defined circumferentially by interior surface 292. A sheath-holding, tube wiper compression applying double wall collar, generally designated 294 is force-fit at its distal outside wall within the hollow interior of the collar 290, after an annular washer 296 is placed within the hollow of the wall 290 so as to abut shoulder 291. The disk or wash, her 296 is preferably formed of yieldable synthetic resinous material, such as silicone rubber, and has an inside diameter at aperture-defining surface 298 so as to compressively engage the exterior surface of the catheter tube 120. Thus, the catheter tube 120 is wiped by surface 298 as it is withdrawn from use in the respiratory system of an intubated medical patient, thereby removing secretions and other materials carried upon the exterior surface of the catheter tube 120 and depositing the same in the wash chamber 274.

The double flange fitting 294 provides a certain amount of radially compressibility, which accommodates ready compression fit insertion within wall 290 with the forward edges of inside collar wall 295 and the outside collar wall 299 holding washer 296 in the illustrated position of FIG. 1 and aperture-defining surface 297 providing guidance to the catheter tube as it is displaced.

In addition, the distal end 302 of a collapsible, preferably transparent, plastic sheath, generally designated 304 is placed over the trailing outside annular collar surface 300 of 295. Sheath end 302 is held in compression-fit relationship by a collar 306 forced over the concentrically disposed end 302 and flange surface 300.

The proximal end of the cartridge 116 comprises seriatim a proximal fitting 320 disposed at the end of the collapsible sleeve or envelope 304, a normally closed suction valve, generally designated 322 and an exteriorally stepped tube, generally designated 324. Fitting 320 is illustrated as being formed as one piece from suitable synthetic resinous material and comprises a trailing or proximal collar 326, the exterior annular surface 328 of which is substantially the same diameter as the diameter of bore 330 forming a part of valve 322. The collar 326 is secured in the position illustrated in FIG. 1 by plastic welding, bonding, or any other suitable fashion.

The hollow interior of collar 326, at radially-directed wall 327 thereof, defines an aperture 332. Fitting 320 also comprises an annular distally-extending interior flange 334, which defines a hollow interior shown as having a uniform diameter extending to aperture 332, into which the trailing end 336 of catheter tube 120 is inserted and secured suitably in the installed position by an appropriate bonding agent, plastic welding, or in any other suitable fashion.

Fitting 320 comprises an exterior, distally-directed flange 338, which is radially spaced from flange 334. The trailing end 342 of the collapsible sheath 304 is contiguously placed over the exterior surface of flange 338, over which a collar 344 is force-fit to retain the end 342 in the assembled position.

When the normally closed valve 322 is manually depressed, negative pressure or suction is delivered from a suitable source along a suction tube to the hollow interior of stepped tube 324 passes across valve 322, through hollow passageways therein, through aperture 332, and along the hollow interior of tube 120 when the distal end of the tube 120 is suitably positioned within a selected lung of the patient. As a consequence, secretions accumulated in the lung are suctioned along the hollow interior of the tube 120 across aperture 332, the hollow interior of the control valve 322 and thence through stepped tube 324.

The control valve 322 comprises a manually actuated reciprocable plunger, generally designated 350, a base plate 354, a female housing member generally designated 356, and a single element elastomeric member, generally designated 358.

Plunger 350 comprises an oval-shaped exposed actuator 360, integrally connected to a rigid, vertically-oriented hollow tube 362, a flange end 364 which is seated in a correspondingly-shaped recess 366 within the hollow interior of the single element 358. Female receptacle 356 comprises a cavity 368, defined by an upwardly-directed oval-shaped flange 370 in which the plunger 350 reciprocates down and up, respectively, when actuator 360 is actuated and released. The female receptacle 356 comprises a distal passageway 372 and a proximal passageway 374, which communicate one with the other across the single element 358 when the actuator 360 is depressed, by reason of the tear-shaped configuration of the single element 358. Element 358 comprises a 360° reverse bend 376, an annular flange 377, and a pear-shaped lower region, the diameter of which varies so that in the up position, the single element 358 seals passageways 372 and 374 preventing delivery of suction to the interior of the catheter tube 120. Flange 377 is anchored in the assembled position by a retainer 379 which is bonded in the position illustrated in FIG. 1. In the down position, communication of negative pressure between passageways 372 and 374 occurs around a reduced diameter part of the teardrop portion of the element 358. Element 358 also serves to inhibit introduction of atmospheric air into the valve because base plate 354 is sealed in position. Element 358 also serves as its own spring, since the element 358 is stretched in a downward direction as the actuator 360 is depressed. Consequently, the memory of the element 358 causes the single element 358 to be returned to the sealed position illustrated in FIG. 1 when manual force on actuator 360 is released.

Stepped tube 324 comprises exterior annular shoulders so that the stepped tube 324 may be inserted into and retained in medical grade tubing. Stepped tube 324 defines an interior bore in communication with bore 374 along which negative pressure is communicated selectively, as described above.

At any desired point in time, the cartridge 116, with the catheter tube 120 retracted, can be manually removed and discarded, following which a fresh cartridge of similar or dissimilar design or purpose can be inserted into the female receptacle 117 defined by wall 112 to assist in providing the appropriate therapy for the patient.

To improve the quality of health care available to intubated patients, it is important to avoid the possibility that ventilating tubing could be twisted and the availability to the patient of ventilating gases either occluded or materially reduced. To achieve this purpose, the swivel fitting provided by previously described rotatable tubes 88 and 88' are provided. More specifically, bell housings 46 and 80 are typically stationary during use, whereas connector tubes 88 and 88' are readily rotated. Accordingly, when tube 88 is compression or otherwise connected to a tracheal tube, for example, the remainder of adapter 44 may rotate as needed to relieve stress, without risking imposition of torque on the tracheal tube. Similarly, when ventilating tubing is force-fit upon or otherwise connected to tube 88', tube 88' may rotate as needed to relieve stress, prevent twisting of the ventilating tubing, and insure a continuing full supply of ventilating gases to the intubated patient.

It is to be appreciated that while the specific configuration comprising adapter 44, illustrated and described in connection with FIG. 1, comprises a single distal port and a plurality of proximal ports, the swivel feature provided by tubes 88 and 88' may be utilized with any type of ventilating fitting, for example the swivel connection may comprise a tee-piece, an elbow, etc.

Other forms of adapters may comprise configurations other than an elbow which embody principles of the present invention.

The invention may be embodied in other specific forms without departing from the spirit of essential characteristics thereof. The present embodiments are therefore to be considered in all respects as illustrative and are not restrictive, the scope of the invention being indicated by the appended claims rather than by the foregoing description, and all changes which come within the meaning and range of equivalency of the claims are therefore intended to be embraced therein.

An embodiment of the invention includes, but is not limited to multi-port fitting for administering respiratory therapy to an intubated medical patient comprising an interiorly hollow main body, such as bell housing 46. The hollow main body comprises a hollow distal part, such as distal female bell housing 46. The hollow distal part defines a distal respiratory flow path and a hollow proximal part, such as second bell housing 80, defining at least one proximal respiratory flow path. A distal tube is rotatably telescopically coupled to the hollow distal part, such as sleeve 88, and a proximal tube, such as sleeve 88', is rotatably telescopically coupled to the hollow proximal part. At least one if not both telescopic couplings comprise a longitudinally-directed rotatable union comprising a sealing structure which comprises at least two spaced annular male ring shaped prongs 102 and 103, each prong extending into and being relatively rotatable within an annular female groove or blind slot 66 and 67.

Another embodiment of the invention is a swivel connection for preventing twisting of a ventilating tube. The swivel connection comprises a first hollow fitting member, illustrated for example by sleeve 88, and a second hollow fitting member, illustrated by bell 46, telescopically overlapping the first hollow fitting member. The connection further comprises a swivel union that comprises at least two spaced annular axially-directed male rings, otherwise denoted as male prongs 102 and 103, each snugly though relatively rotatably disposed in a matching annular axially-directed female groove or blind slot 66 and 67.

Another embodiment of the invention includes connection for preventing twisting of a ventilating tube. The connection comprises a first hollow fitting member, sleeve 88, and a second hollow fitting member, bell 46, telescopically overlapping the first hollow fitting member so that the hollows of the two members are in alignment to define a common flow path. The connection further comprises a union that comprises (1) structure for preventing significant axial misalignment of the hollows of the two members, (2) structure for preventing significant axial displacement of one member in respect to the other member, and (3) structure creating at least four radially juxtaposed sealing sites to prevent entry of atmospheric material between the two members into either hollow. The creating structure of the union comprises at least two juxtaposed male rings 102 and 103 of one member each rotatably seated contiguously in a female annular recess (blind slots 66 and 67) of the other member. Each of the male rings comprise a blunt edge comprising two sealing sites. The creating structure to prevent entry of atmospheric material may also comprise an annular sleeve in the nature of a bushing non-rotatably secured to one member comprising a bell housing 4b. The bushing contiguously rotatably engages both a surface of a male annulus, such as flange 105, and another surface area of the other member, sleeve 88.

Another embodiment of the invention is a closed system respiratory adapter comprising structure defining a distal female receptacle comprising a distal port 32, and structure defining at least two proximal female receptacles 34 and 36, each comprising a proximal port. One of said proximal female receptacles 34 comprises wall structure for receiving a distal end of a unitary aspirating catheter assembly in releasibly, replaceable, compression-fit relation. The second of said proximal female receptacles 36 comprises swivel wall structure for receiving a distal end of ventilating tubing 89'. The distal female receptacle 32 and the second proximal female receptacle 36 each comprises swivel wall structure for releasible connection directly or indirectly to a tracheal tube 89. Each swivel wall structure comprising at least two spaced seal members, or male prongs 102, to prevent entry of atmosphere across the swivel wall structure. The respiratory adapter may have an elbow configuration.

Another embodiment of the invention is a closed tracheal assembly comprising a hollow tracheal tube 89. The assembly comprises a distal end for placement in the respiratory tract and a proximal end for external availability. A hollow adapter 44 comprises a distal end by which the adapter is connected to the proximal end of the tracheal tube through port 32. The distal end of the adapter further comprising swivel structure comprising at least two interfit relatively rotatable male/female connections, i.e. male prongs 102 and 103 and female blind slots 66 and 67, each defining spaced anti-atmospheric infiltration sealing sites.

Another embodiment of the invention is a closed tracheal assembly comprising a hollow tracheal tube 89 comprising a distal end for placement in the respiratory tract and a proximal end for external availability, and a hollow adapter 44 comprising a distal end by which the adapter is connected to the proximal end of the tracheal tube. The distal end of the adapter further comprises a proximal end through which a ventilating gas is delivered to the respiratory tract, the proximal end swivel structure comprising at least two interfit relatively rotatable male/female connections each defining spaced anti-atmospheric infiltration sealing sites.

Another embodiment of the invention is a connection for preventing twisting of a ventilating tube, the connection comprising a first hollow fitting member and a second hollow firing member telescopically overlapping the first hollow fitting member so that the hollows of the two members are in alignment defining a common flow path. The connection further comprises a union that comprises structure preventing significant axial misalignment of the hollows of the two members. The structure prevents significant axial displacement of one member in respect to the other member and structure creating at least four spaced through radially juxtaposed sealing sites (20, 22, 24, and 26) between pairs of intermeshed male and female portions to prevent entry of atmospheric material between the two members into either hollow.

What is claimed and desired to be secured by Letters Patent is:

1. An adaptor for coupling an intubated patient tube to exterior tubing, comprising:

a main body portion defining a flow path therethrough that is adapted for providing fluid flow between an intubated patient tube and exterior tubing, said main body portion comprising a first end adapted for connection to the intubated patient tube and a second end adapted for connection to the exterior tubing;

sleeve means for providing a swivel coupling for joining at least one of the intubated patient tube and the exterior tubing to at least one of said ends of the main body portion, such that when joined the sleeve means is fully rotatable in any direction about its entire circumference without becoming disconnected from the main body portion; and sealing means for providing an essentially hermetic seal between said fully rotatable sleeve means and said at least one of said ends of the main body portion, said sealing means comprising at least one continuously annular sealing rib means and an adjacent wall, with the rib means held in a continuously radially deflected position while said sleeve means is connected with said at least one of said ends of the main body portion so as to contact the adjacent wall in order to form a sealing site with the adjacent wall when the rib means is deflected.

2. An adaptor for coupling an intubated patient tube to exterior tubing as recited in claim 1 further comprising collar means for retaining said sleeve means so as to prevent separation of said sleeve means from the at least one of said ends of the main body portion.

3. An adaptor for coupling an intubated patient tube to exterior tubing as recited in claim 1 wherein said sleeve means provides a swivel coupling for joining the intubated patient tube to said first end of said main body portion and wherein said adaptor further comprising a second sleeve means for providing a swivel coupling for joining the exterior tubing to said second end of said main body portion.

4. An adaptor for coupling an intubated patient tube to exterior tubing as recited in claim 3 further comprising:

a first collar means for retaining said sleeve means so as to prevent separation of said sleeve means from said first end of said main body portion; and a second collar means for retaining said second sleeve means so as to prevent separation of said sleeve means from said second end of said main body portion.

5. An adaptor for coupling an intubated patient tube to exterior tubing as recited in claim 1 further comprising barrel means adapted for connection to catheter cartridge means.

6. An adaptor for coupling an intubated patient tube to exterior tubing as recited in claim 1 wherein said sealing means comprises a plurality of sealing rib means and a plurality of adjacent walls, with the plurality of rib means held in a radially deflected position so as to contact at least one of the plurality of adjacent walls in order to form at least one sealing site with said at least one of the plurality of adjacent walls when said plurality of rib means is deflected.

7. An adaptor for coupling an intubated patient tube to exterior tubing, comprising:

a main body portion defining a flow path therethrough that is adapted for providing fluid flow between an intubated patient tube and exterior tubing, said main body portion comprising a first end adapted for connection to the intubated patient tube and a second end adapted for connection to the exterior tubing;

first sleeve means for providing a swivel coupling joined between the intubated patient tube and the first end of the main body portion, such that when joined the first sleeve means is fully rotatable in any direction about its entire circumference without becoming disconnected from the main body portion;

second sleeve means for providing a swivel coupling joined between the exterior tubing and the second end of the main body portion, such that when joined the second sleeve means is fully rotatable in any direction about its entire circumference without becoming disconnected from the main body portion; and first sealing means for providing an essentially hermetic seal between said fully rotatable first sleeve means and said first end of the main body portion, and second sealing means for providing an essentially hermetic seal between said fully rotatable second sleeve means and said second end of the main body portion, each of said sealing means comprising at least one continuously annular sealing rib means and an adjacent wall, with the rib means of said first sealing means held in a continuously radially deflected position while said first sleeve means is connected with said first end of the main body portion so as to contact the adjacent wall in order to form a sealing site with the adjacent wall when the rib means is deflected and with the rib means of said second sealing means held in a continuously radially deflected position while said second sleeve means is connected with said second end of the main body portion so as to contact the adjacent wall in order to form a sealing site with the adjacent wall when the rib means is deflected.

8. An adaptor for coupling an intubated patient tube to exterior tubing as recited in claim 7 wherein the first sleeve means comprises a first swivel sleeve and wherein the second sleeve means comprises a second swivel sleeve.

9. An adaptor for coupling an intubated patient tube to exterior tubing as recited in claim 8 wherein the at least one sealing rib means comprises at least one sealing rib.

10. An adaptor for coupling an intubated patient tube to exterior tubing as recited in claim 9 comprising barrel means adapted for connection to catheter cartridge means.

11. An adaptor for coupling an intubated patient tube to exterior tubing as recited in claim 10 comprising:

a first collar means for retaining said first sleeve means so as to prevent separation of said sleeve means from said first end of said main body portion; and a second collar means for retaining said second sleeve means so as to prevent separation of said sleeve means from said second end of said main body portion.

12. An adaptor for coupling an intubated patient tube to exterior tubing as recited in claim 11 wherein said barrel means comprises a proximally extending barrel adapted for connection to catheter cartridge means.

13. An adaptor for coupling an intubated patient tube to exterior tubing as recited in claim 12 wherein said first collar means comprises a first annular collar received within the first end of the main body portion and wherein said second collar means comprises a second annular collar received within said second end of the main body portion.

14. An adaptor for coupling an intubated patient tube to exterior tubing, comprising:

a main body portion defining a flow path therethrough that is adapted for providing fluid flow between an intubated patient tube and exterior tubing, said main body portion comprising a first end adapted for connection to the intubated patient tube and a second end adapted for connection to the exterior tubing;

a first swivel sleeve having one end joined to the intubated patient tube and having a second end joined to said first end of the main body portion, said joined ends of the first swivel sleeve and the body portion together forming at least one continuously annular sealing rib and an adjacent wall, with the sealing rib held in a continuously radially deflected position while said first end of the main body portion and said first swivel sleeve are connected together so as to contact the adjacent wall in order to form a sealing site with the adjacent wall when the sealing rib is deflected, such that when joined the first swivel sleeve is essentially hermetically sealed to the body portion and yet is still fully rotatable in any direction about its entire circumference without becoming disconnected from the main body portion; and a second swivel sleeve having a first end joined to the exterior tubing and having a second end joined to said second end of the main body portion, said joined ends of the second swivel sleeve and the body portion together forming at least one continuously annular sealing rib and an adjacent wall, with the sealing rib held in a continuously radially deflected position while said first end of the main body portion and said second swivel sleeve are connected together so as to contact the adjacent wall in order to form a sealing site with the adjacent wall when the sealing rib is deflected, such that when joined the second swivel sleeve is essentially hermetically sealed to the body portion and yet is still fully rotatable in any direction about its entire circumference without becoming disconnected from the main body portion.

15. An adaptor for coupling an intubated patient tube to exterior tubing, comprising:

a main body portion defining a flow path therethrough that is adapted for providing fluid flow between an intubated patient tube and exterior tubing, said main body portion comprising a first end adapted for connection to the intubated patient tube and a second end adapted for connection to the exterior tubing;

sleeve means for providing a swivel coupling for joining at least one of the intubated patient tube and the exterior tubing to at least one of said ends of the main body portion, such that when joined the sleeve means is fully rotatable in any direction about its entire circumference without becoming disconnected from the main body portion; and sealing means for providing an essentially hermetic seal between said fully rotatable sleeve means and said at least one of said ends of the main body portion, said sealing means comprising a plurality of radially spaced continuously annular sealing sites formed by a plurality of radially spaced matching continuous annular male and female sealing members, with at least one of said plurality of annular male and female sealing members being in a continuously radially deflected position while said sleeve means and said main body portion are connected.

\* \* \* \* \*